(12) United States Patent
Lee et al.

(10) Patent No.: US 12,053,286 B2
(45) Date of Patent: Aug. 6, 2024

(54) GRIP STRENGTH MEASUREMENT APPARATUS

(71) Applicant: DAEGU GYEONGBUK INSTITUTE OF SCIENCE AND TECHNOLOGY, Daegu (KR)

(72) Inventors: Sungwon Lee, Dangjin-si (KR); Nora Asyikin Binti Zulkifli, Daegu (KR); Wooseong Jeong, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 354 days.

(21) Appl. No.: 17/638,456

(22) PCT Filed: Jul. 14, 2020

(86) PCT No.: PCT/KR2020/009263
§ 371 (c)(1),
(2) Date: Feb. 25, 2022

(87) PCT Pub. No.: WO2021/040230
PCT Pub. Date: Mar. 4, 2021

(65) Prior Publication Data
US 2022/0346688 A1  Nov. 3, 2022

(30) Foreign Application Priority Data

Aug. 26, 2019  (KR) .......................... 10-2019-0104383

(51) Int. Cl.
*A61B 5/22* (2006.01)
*G01L 1/12* (2006.01)
(52) U.S. Cl.
CPC ................ *A61B 5/225* (2013.01); *G01L 1/12* (2013.01); *A61B 2562/0223* (2013.01); *A61B 2562/164* (2013.01)

(58) Field of Classification Search
CPC ............ A61B 5/225; A61B 2562/0223; A61B 2562/164; A63B 23/16; G01L 1/12; G01L 1/122
See application file for complete search history.

(56) References Cited

U.S. PATENT DOCUMENTS

| 5,317,916 | A | * | 6/1994 | Kovacevic | ............. | A63B 23/16 |
| | | | | | | 73/379.03 |
| 2016/0265985 | A1 | * | 9/2016 | Onal | ....................... | G01L 5/226 |
| 2019/0038205 | A1 | * | 2/2019 | Gold | ....................... | A61B 5/225 |

FOREIGN PATENT DOCUMENTS

| CA | 2676672 A1 * | 8/2008 | ......... A61B 5/04888 |
| JP | 2002-345794 A | 12/2002 | |

(Continued)

OTHER PUBLICATIONS

Korean Notice of Allowance for application No. 10-2019-0104383 dated Mar. 30, 2021.

(Continued)

*Primary Examiner* — Francis C Gray
(74) *Attorney, Agent, or Firm* — Pearne & Gordon LLP

(57) ABSTRACT

The present invention relates to a device for measuring grip strength including a basis; a cover coupled to the basis to form an enclosed pressure space separated from the outside; a cap disposed between the basis and the cover and configured to form a sensing space separated from the pressure space; magnets mounted on the cap or the basis to form a magnetic field; and a magnetic sensor for detecting change in the magnetic field. With this configuration, when measuring the grip strength of the user's hand, accuracy or sensitivity may be increased.

20 Claims, 10 Drawing Sheets

(56) References Cited

FOREIGN PATENT DOCUMENTS

| | | |
|---|---|---|
| KR | 10-2009-0029157 A | 3/2009 |
| KR | 20-2009-0003372 U | 4/2009 |
| KR | 10-10772322 B1 | 10/2011 |
| KR | 10-2014-0121631 A | 10/2014 |
| WO | WO-2019076937 A1 * | 4/2019 |

OTHER PUBLICATIONS

International Search Report PCT/ISA/210 for International Application No. PCT/KR2020/009263 dated Mar. 11, 2021.

* cited by examiner

[FIG. 1]
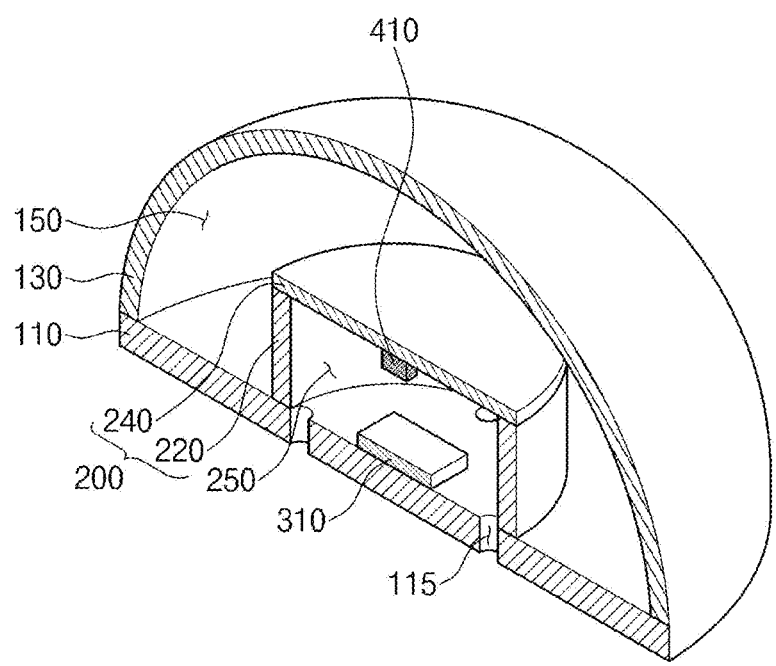

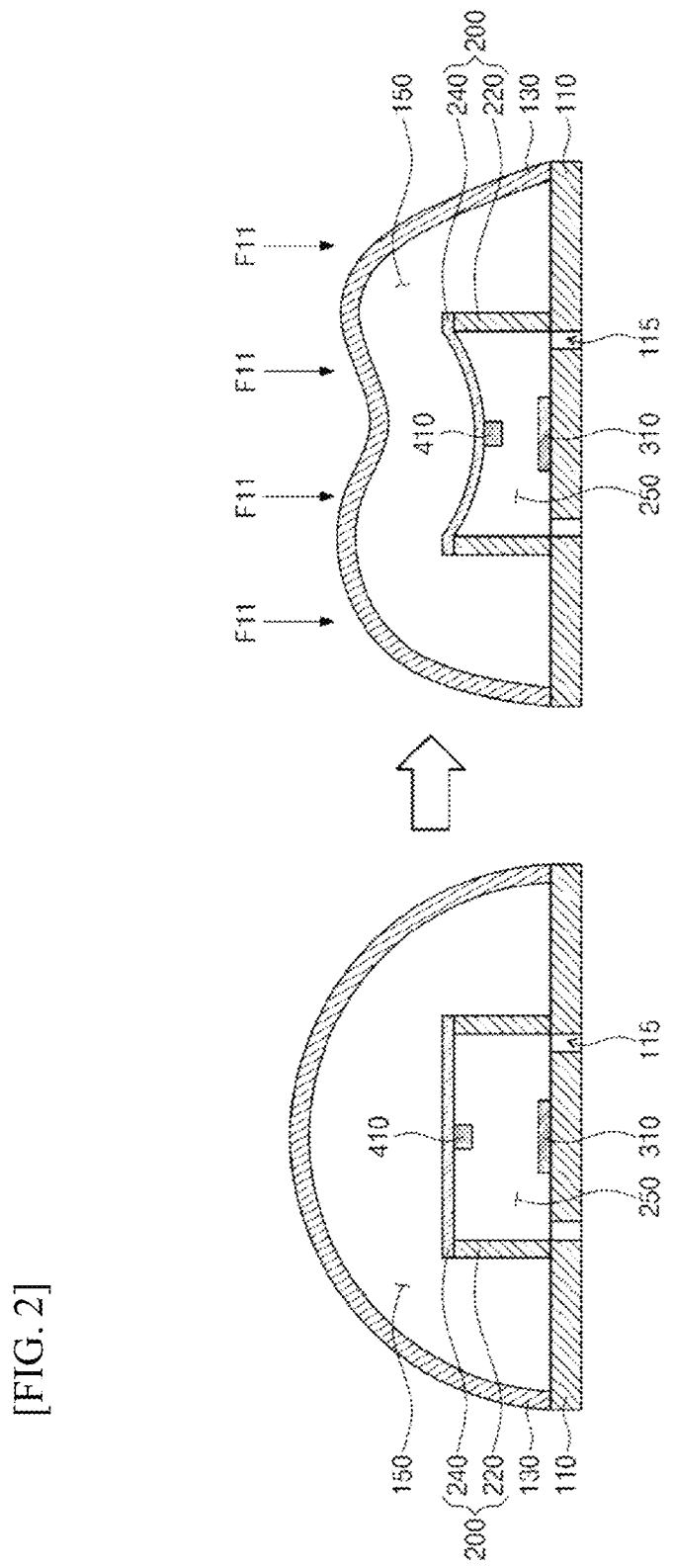
[FIG. 2]

[FIG. 3]
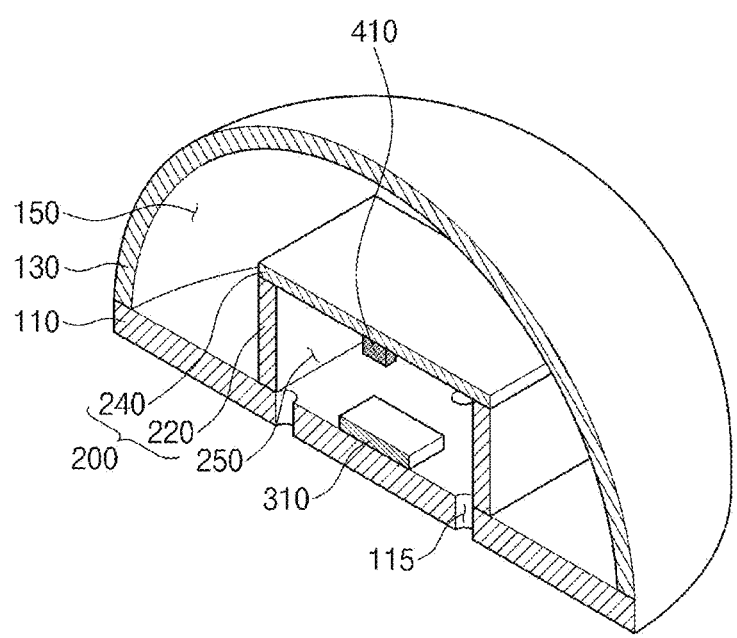

[FIG. 4]
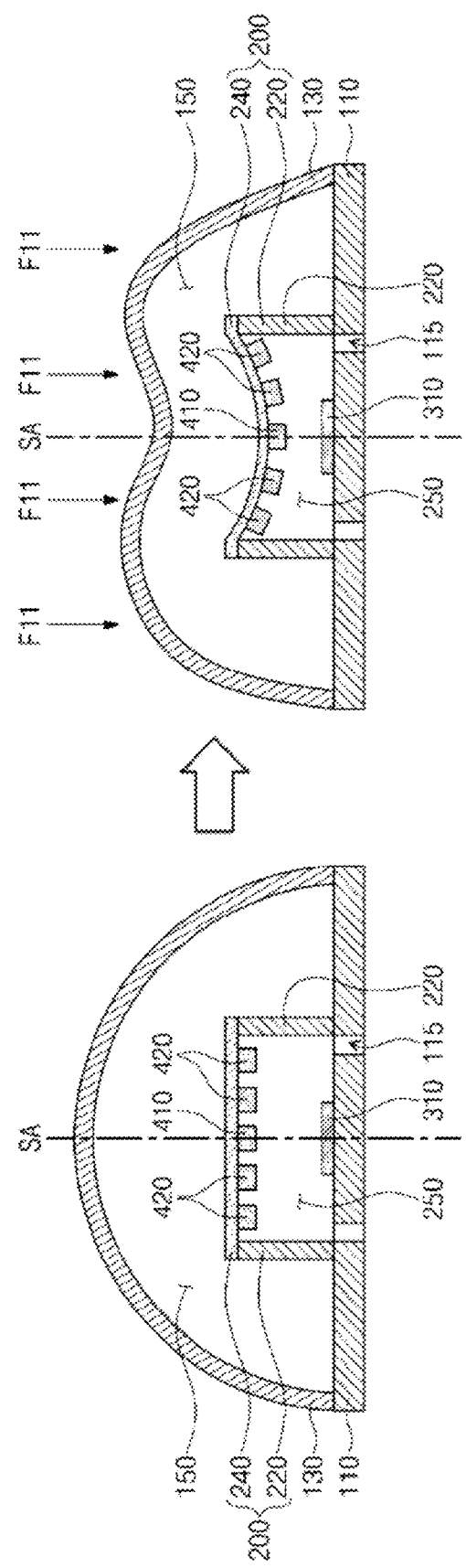

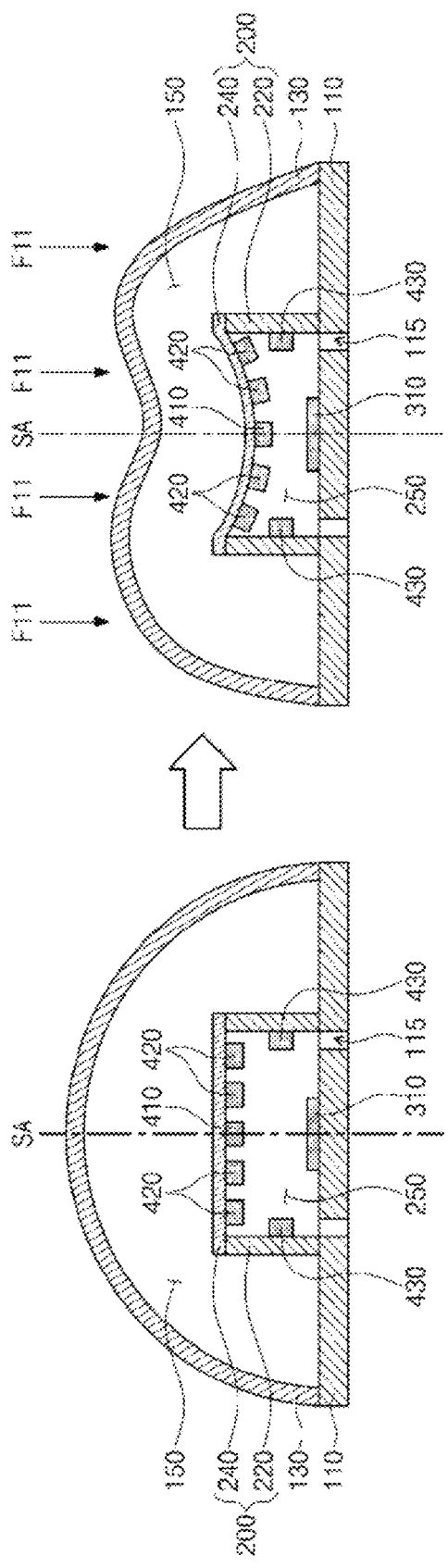
[FIG. 5]

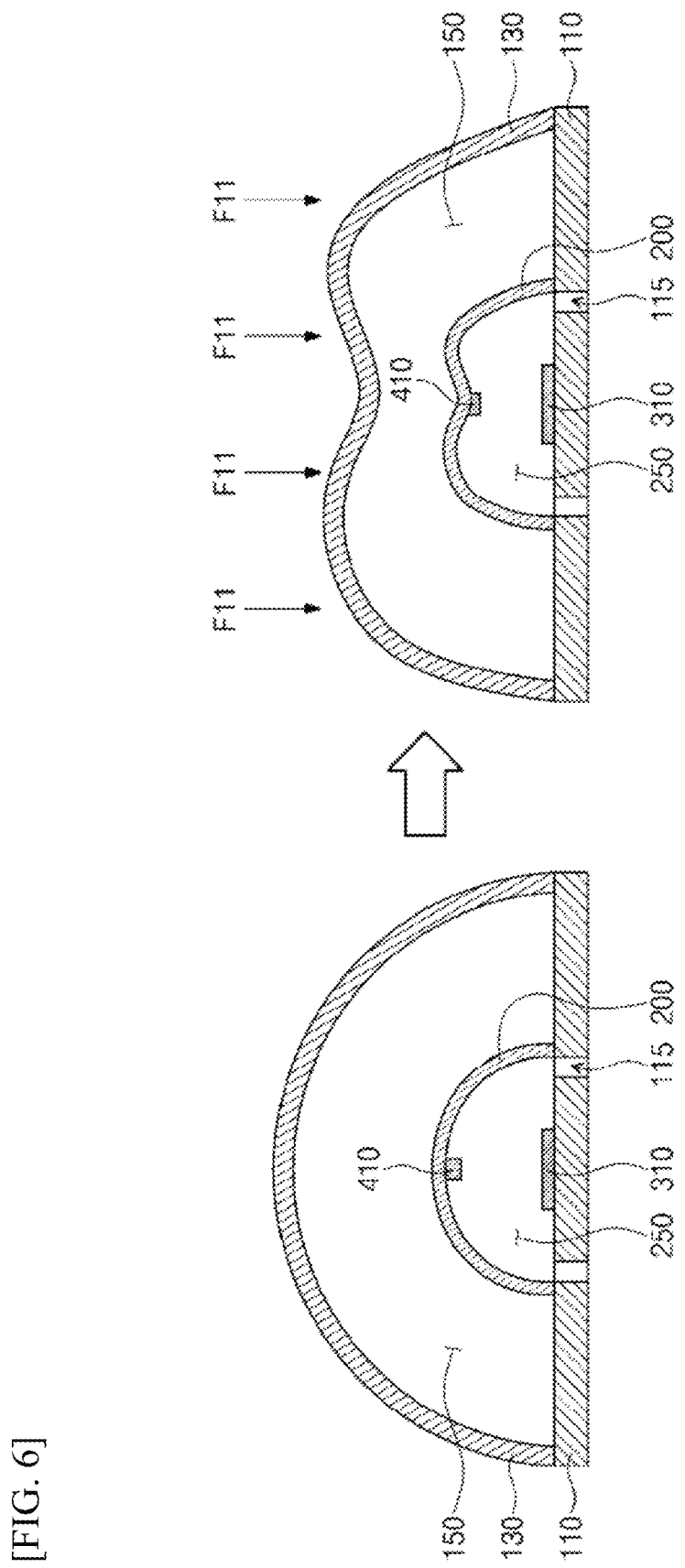
[FIG. 6]

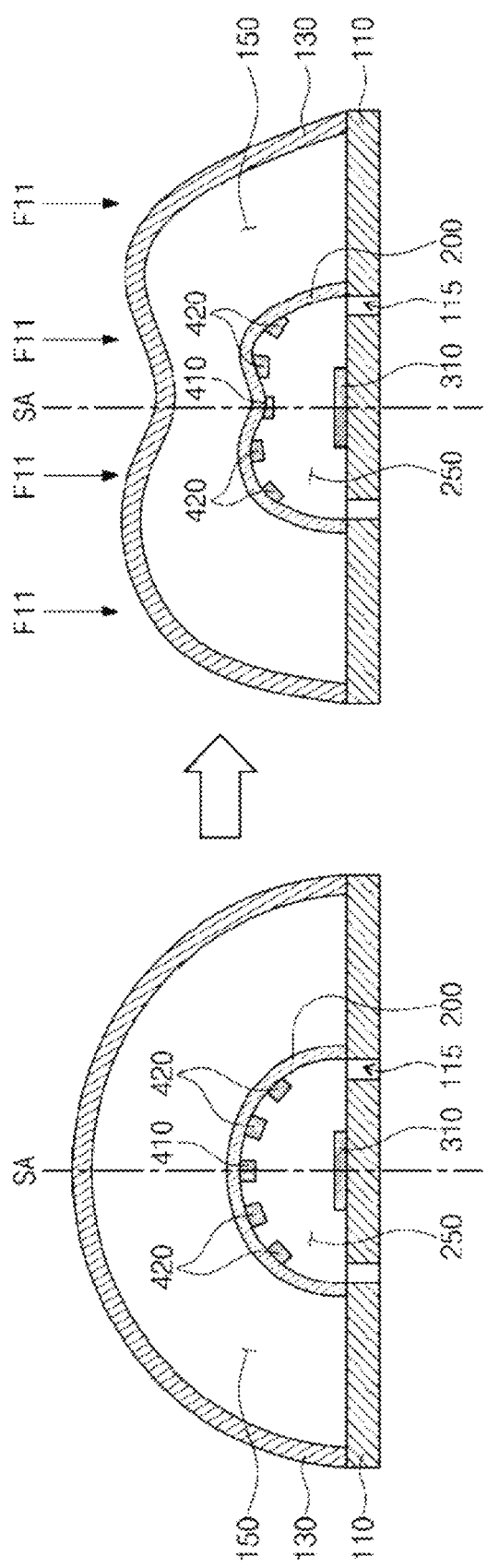
[FIG. 7]

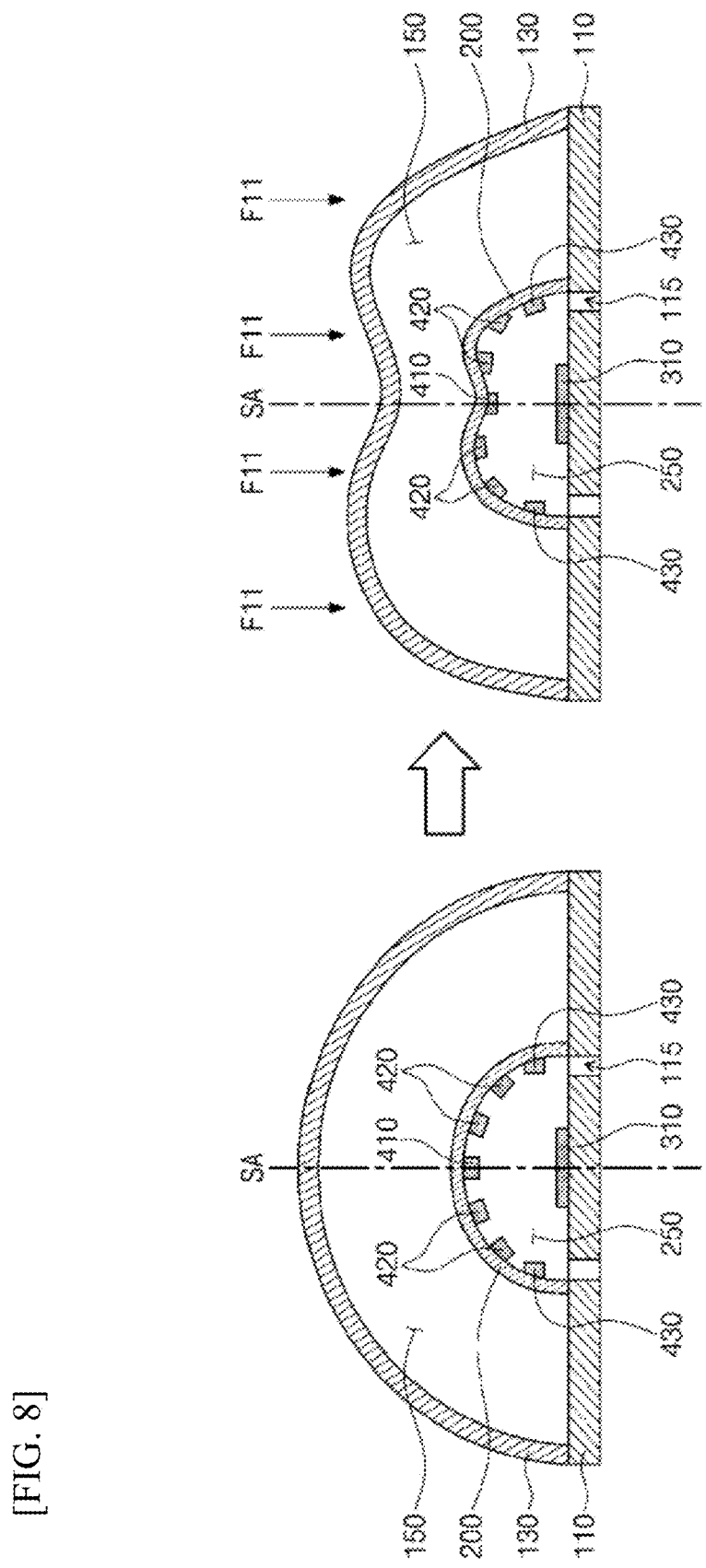
[FIG. 8]

[FIG. 9]
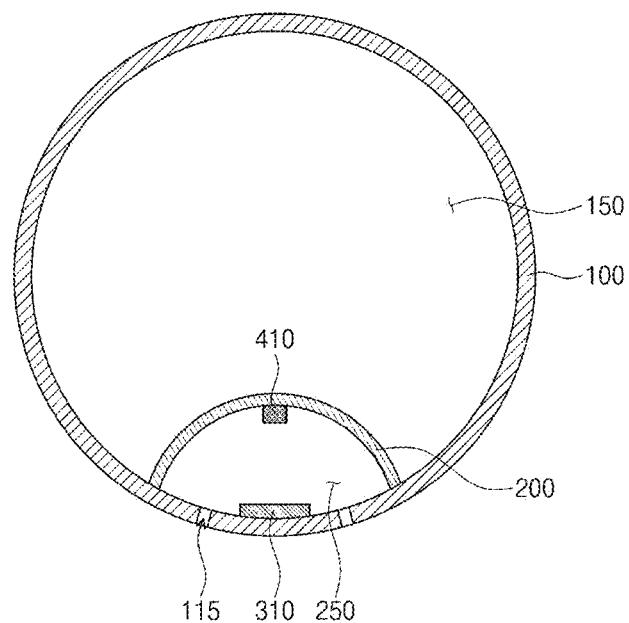
[FIG. 10]
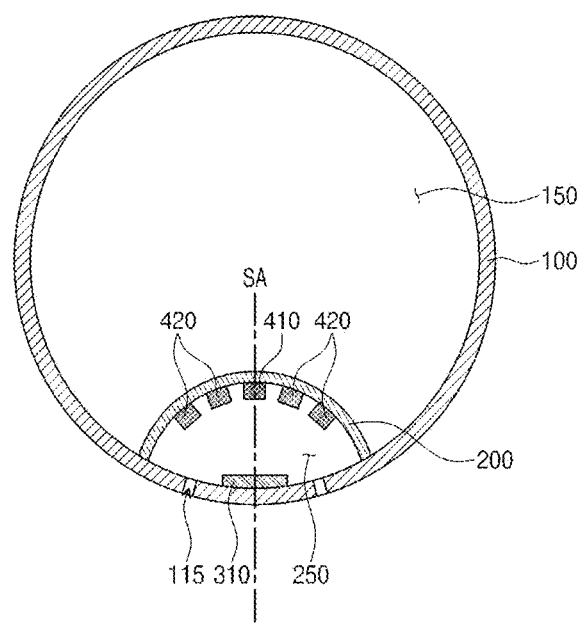

[FIG. 11]
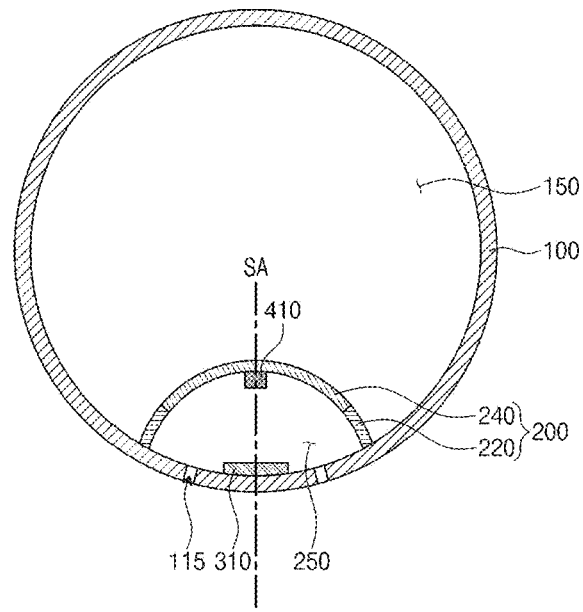
[FIG. 12]
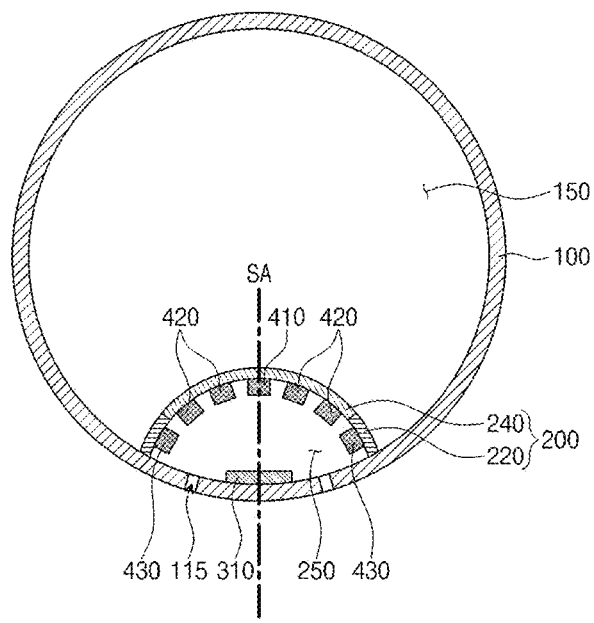

GRIP STRENGTH MEASUREMENT APPARATUS

CROSS-REFERENCE TO RELATED APPLICATION

This application is a National Stage Entry of PCT International Application No. PCT/KR2020/009263, which was filed on Jul. 14, 2020, and claims priority to Korean Patent Application No. 10-2019-0104383, filed on Aug. 26, 2019 in the Korean Intellectual Property Office, the disclosure of which is incorporated herein by reference.

TECHNICAL FIELD

The present invention relates to a device for measuring grip strength, which is force applied by a person's hand.

BACKGROUND ART

To restore the function of a lost or congenitally weakened musculoskeletal system, various rehabilitation medical devices have been developed. The rehabilitation medical devices are widely used for medical rehabilitation of the elderly, congenital premature babies, and the disabled, and help them lead smooth social activities.

As an example of such a rehabilitation medical device, there is a grip strength measuring device for measuring the grip strength of the hand, restoring the function of the musculoskeletal system of the hand, and helping the rehabilitation.

The purpose of the grip strength measuring device is to help rehabilitation or recovery by measuring the grip strength of the hand more accurately to restore the function of the hand. Accordingly, an important requirement for the grip strength measuring device is to accurately measure grip strength.

In this regard, Korean Patent No. 10-1077232 (hereinafter referred to as the related art document) has been disclosed. The related art document relates to a grip strength measuring device including two measuring bars; a force sensor attached to the outer side of the two measuring bars to sense the force of the thumb and the index finger; a motor for moving the two measuring bars in opposite directions using driving force; and a controller for controlling the operation of the motor.

However, according to the related art document, there is a problem in that grip strength measurement is limited only to the thumb and the index finger. Due to this limitation, when the grip strength measuring device is not accurately gripped, measurement accuracy is reduced.

Therefore, a technology capable of ensuring the accuracy of hand grip strength measurement is required.

DISCLOSURE

Technical Problem

Therefore, the present invention has been made in view of the above problems, and it is one object of the present invention to provide a device for measuring grip strength capable of accurately measuring grip strength applied by a user.

Technical Solution

In accordance with one aspect of the present invention, provided is a device for measuring grip strength including a basis; a cover coupled to the basis to form an enclosed pressure space separated from outside, wherein an outer shape of the cover is elastically changed by grip strength; a cap disposed between the basis and the cover and coupled to the basis to form a sensing space separated from the pressure space; magnets mounted on the cap or the basis to form a magnetic field in the sensing space; and a magnetic sensor mounted on the cap or the basis to detect change in the magnetic field formed by the magnet.

Here, the cap may include a boundary wall having a lower end coupled to the basis to secure the sensing space; and a roof coupled to an upper end of the boundary wall to separate the sensing space and the pressure space, and on which the magnets or the magnetic sensor is mounted.

Here, at least a portion of the cap may have a curved shape or a dome shape, and may be made of a material that is elastically deformable.

Here, exhaust holes for communicating the sensing space with an outside may be provided in the basis to change a volume of the sensing space.

Here, the device for measuring grip strength may have any one arrangement structure of an arrangement structure in which the magnets are mounted on the cap and the magnetic sensor is mounted on the basis and an arrangement structure in which the magnets are mounted on the basis and the magnetic sensor is mounted on the cap, so that the magnets and the magnetic sensor are disposed to face each other.

Here, the magnets may be provided in plural, and any one of the magnets may be disposed to face the magnetic sensor; and the magnets may be arranged to be axially symmetric with respect to an imaginary axis of symmetry connecting the magnet facing the magnetic sensor and the magnetic sensor.

Here, the magnets may be provided in plural, and the magnets may be disposed to be spaced apart from each other by a predetermined interval.

Here, the device for measuring grip strength may have any one arrangement structure of an arrangement structure in which the magnets are mounted on the roof and the magnetic sensor is mounted on the basis and an arrangement structure in which the magnets are mounted on the basis and the magnetic sensor is mounted on the roof, so that the magnets and the magnetic sensor are disposed to face each other, wherein the magnets are provided in plural, and one or more of the magnets are disposed on the boundary wall.

Here, the boundary wall of the cap may be made of a material having elasticity and ductility to be elastically deformed by external force.

Here, the roof may be made of a material having elasticity and ductility to be elastically deformed by external force, and the boundary wall may be made of a material having hardness to suppress deformation due to external force.

In accordance with another aspect of the present invention, provided is a device for measuring grip strength including a housing having an outer shape that is elastically changed by grip strength applied when gripped by a user's hand, wherein an enclosed pressure space separated from outside is formed in the housing to maintain internal pressure; a cap coupled to an inside of the housing to form a sensing space separated from the pressure space; magnets mounted on the cap or the housing to form a magnetic field in the sensing space; and a magnetic sensor mounted on the cap or the housing to be spaced apart from the magnets, and configured to detect change in the magnetic field according to change in position or posture relative to the magnets.

Here, at least a portion of the cap may have a dome shape, and may be made of a material having elasticity.

Here, the cap may include a boundary wall having a lower end coupled to an inside of the housing to secure the sensing space and separate the magnets and the magnetic sensor; and a roof coupled to an upper end of the boundary wall to separate the sensing space and the pressure space, and on which the magnets or the magnetic sensor is mounted.

Here, exhaust holes for communicating the sensing space with an outside may be provided in the housing so that a volume of the sensing space is changed.

Here, the device for measuring grip strength may have any one arrangement structure of an arrangement structure in which the magnets are mounted on the cap and the magnetic sensor is mounted on the housing and an arrangement structure in which the magnets are mounted on the housing and the magnetic sensor is mounted on the cap, so that the magnets and the magnetic sensor are disposed to face each other.

Here, the magnets may be provided in plural, and any one of the magnets may be disposed to face the magnetic sensor; and the magnets may be arranged to be axially symmetric with respect to an imaginary axis of symmetry connecting the magnet facing the magnetic sensor and the magnetic sensor.

Here, the magnets may be provided in plural, and the magnets may be disposed to be spaced apart from each other by a predetermined interval.

Here, the device for measuring grip strength may have any one arrangement structure of an arrangement structure in which the magnets are mounted on the roof and the magnetic sensor is mounted on the basis and an arrangement structure in which the magnets are mounted on the basis and the magnetic sensor is mounted on the roof, so that the magnets and the magnetic sensor are disposed to face each other, wherein the magnets are provided in plural, and one or more of the magnets are disposed on the boundary wall.

Here, the boundary wall of the cap may be made of a material having elasticity and ductility to be elastically deformed by external force.

Here, the roof of the cap may be made of a material having elasticity and ductility to be elastically deformed by external force, and the boundary wall of the cap may be made of a material having hardness to suppress deformation due to external force.

Advantageous Effects

Since a device for measuring grip strength according to the present invention senses magnetic field change caused by grip strength applied by the hand, ease and accuracy can be secured when measuring grip strength.

DESCRIPTION OF DRAWINGS

FIG. 1 is a schematic perspective cross-sectional view of a device for measuring grip strength according to one embodiment of the present invention.

FIG. 2 is a schematic side cross-sectional view of a device for measuring grip strength according to one embodiment of the present invention.

FIG. 3 is a schematic perspective cross-sectional view of a device for measuring grip strength according to one embodiment of the present invention, illustrating another exemplary form of a boundary wall and a roof constituting a cap.

FIG. 4 is a schematic side cross-sectional view of a device for measuring grip strength according to one embodiment of the present invention, illustrating an exemplary form in which a plurality of magnets is arranged.

FIG. 5 a schematic side cross-sectional view of a device for measuring grip strength according to one embodiment of the present invention, illustrating another exemplary form in which a plurality of magnets is arranged.

FIG. 6 is a schematic side cross-sectional view of a device for measuring grip strength according to another embodiment of the present invention.

FIGS. 7 and 8 each are a schematic side cross-sectional view of a device for measuring grip strength according to another embodiment of the present invention, illustrating an exemplary form in which a plurality of magnets is arranged.

FIG. 9 is a schematic side cross-sectional view of a device for measuring grip strength according to an applied embodiment of the present invention.

FIG. 10 schematically illustrates an exemplary form in which a plurality of magnets is arranged in a device for measuring grip strength according to an applied embodiment of the present invention.

FIG. 11 is a schematic side cross-sectional view of a device for measuring grip strength according to a modified embodiment of the present invention.

FIG. 12 is a schematic side cross-sectional view of a device for measuring grip strength according to a modified embodiment of the present invention, illustrating an exemplary form in which a plurality of magnets is arranged.

BEST MODE

Hereinafter, the present invention will be described in detail by explaining exemplary embodiments of the invention with reference to the attached drawings. When describing the present invention with reference to the drawings, the same or corresponding components are denoted by the same reference numerals.

FIG. 1 is a schematic perspective cross-sectional view of a device for measuring grip strength according to one embodiment of the present invention, and FIG. 2 is a schematic side cross-sectional view of a device for measuring grip strength according to one embodiment of the present invention.

Referring to FIGS. 1 and 2, a device for measuring grip strength according to one embodiment of the present invention includes a basis 110, a cover 130, a magnet 410, a magnetic sensor 310, and a cap 200 consisting of a roof 240 and a boundary wall 220. The device for measuring grip strength according to the present invention may be used to measure the grip strength of a premature infant to help rehabilitation of the musculoskeletal system of the hand, but the present invention is not limited thereto.

The basis 110 has a predetermined size to be held in the user's hand.

The basis 110 is coupled to the cover 130 to form a pressure space 150.

In addition, the basis 110 is coupled to the cap 200 to support the cap 200. As shown in the drawings, a form in which the boundary wall 220 of the cap 200 is coupled to the basis 110 is also possible. In addition, the basis 110 supports the magnetic sensor 310 or the magnet located inside the cap 200 and mounted on the basis 110. In the drawings, an example in which the magnetic sensor 310 is mounted on the basis 110 is shown.

In addition, exhaust holes 115 through which air is exhausted from a sensing space 250 provided inside the cap 200 are formed in the basis 110.

The basis 110 is preferably made of a flexible material having elasticity, and may also be made of a hard material having hardness.

The cover 130 is coupled to the basis 110 to form the enclosed pressure space 150 separated from the outside.

Preferably, the outer shape of the cover 130 is elastically deformed by grip strength applied by the user's hand. Accordingly, the cover 130 is preferably made of a polymer having elasticity as a main material.

The cap 200 is disposed between the basis 110 and the cover 130 and is coupled to the basis 110 to form the sensing space 250 separated from the pressure space 150. The cap 200 includes the boundary wall 220 and the roof 240.

As shown in the drawings, the lower ends of the boundary wall 220 are coupled to the basis 110 to secure the sensing space 250 and to separate the magnet 410 and the magnetic sensor 310 from each other.

In addition, the roof 240 is coupled to the upper end of the boundary wall 220 to separate the sensing space 250 and the pressure space 150 from each other, and the magnet 410 or the magnetic sensor 310 is mounted thereon.

FIGS. 1 and 2 show an example in which the magnet 410 is mounted on the roof 240 and the magnetic sensor 310 is mounted on the basis 110.

As shown in FIG. 1, the cap may have a cylindrical shape.

In addition, the cap including the boundary wall 220 and the roof 240 may have the following shape.

FIG. 3 is a schematic perspective cross-sectional view of the device for measuring grip strength according to one embodiment of the present invention, showing another exemplary form of the boundary wall 220 and the roof 240 of the cap 200.

Referring to FIG. 3, the overall shape of the cap 200 including the boundary wall 220 and the roof 240 may be a hexahedron, or the cap 200 may be formed so that the sensing space 250 inside the cap 200 has a hexahedral shape.

In addition, it is also preferable that at least a portion of the cap 200 including the boundary wall 220 and the roof 240 has a curved shape or a dome shape.

In addition, the cap 200 is preferably made of an elastic material so that the cap 200 is elastically deformed by external force transmitted through air pressure in the pressure space 150.

For example, the roof 240 of the cap 200 is preferably made of a material having elasticity and ductility so that the roof 240 is elastically deformed by external force, and the boundary wall 220 of the cap 200 is preferably made of a material having hardness to suppress deformation due to external force.

Alternatively, it is also preferable that the roof 240 and the boundary wall 220 of the cap 200 are made of a material having elasticity and ductility so that the roof 240 and the boundary wall 220 are elastically deformed by external force.

In addition, the roof 240 of the cap 200 that is elastically deformable may be made of the same material as the cover 130.

Preferably, the exhaust holes 115 for communicating the sensing space 250 with the outside are provided in the basis 110 so that the volume of the sensing space 250 formed by the cap 200 including the boundary wall 220 and the roof 240 is changed.

When the cover 130 receiving grip strength applied by a user is deformed inward, due to air pressure inside the pressure space 150, which is an enclosed space, force is applied toward the sensing space 250, which is the inside of the cap including the boundary wall 220 and the roof 240.

Preferably, air in the sensing space 250 is exhausted to the outside so that the sensing space 250 is elastically deformed by air pressure in the pressure space 150. Accordingly, air in the sensing space 250 may be exhausted to the outside through the exhaust holes 115 formed in the basis 110.

When the exhaust holes 115 are formed in plural, the exhaust holes 115 may be formed in the basis 110 to be form a uniform arrangement. A configuration in which a plurality of exhaust holes 115 is formed in the basis 110 symmetrically with respect to the magnetic sensor 310 mounted on the basis 110 is also possible.

The magnet 410 is mounted on the roof 240 of the cap 200 or the basis 110 to form a magnetic field in the sensing space 250.

The magnetic sensor 310 is mounted on the roof 240 of the cap 200 or the basis 110, and detects change in a magnetic field formed by the magnet 410. When grip strength of a user is applied to the cover 130, the cap 200 receives force due to air pressure in the sealed pressure space 150. As the cap 200 receives force, the cap 200 is deformed inwardly and the volume of the sensing space 250 is reduced.

At this time, since air in the sensing space 250 is exhausted through the exhaust holes 115, the degree of elastic deformation of the cap 200 may be increased in proportion to the strength of applied force. In addition, since the cap 200 is deformed by force, the distance or the positional posture between the magnetic sensor 310 and the magnet 410 is changed.

Here, the positional posture may be referred to as a posture according to the directions in which the magnetic poles of the magnet 410 are oriented. For example, when the magnetic sensor 310 has a posture in which the directions of the magnetic poles are changed according to deformation of the cap 200 from the posture in which the magnetic poles of the magnet 410 are oriented, this indicates that the positional posture is changed. Accordingly, change of a positional posture may include change of a position and change of an orientation direction.

As the distance or positional posture between the magnetic sensor 310 and the magnet 410 is changed, the magnetic sensor 310 detects change in a magnetic field. The magnetic sensor 310 detects the degree of change in a magnetic field, and based on this detection, user's grip strength may be measured.

Accordingly, preferably, the magnet 410 is mounted on the roof 240 of the cap 200 and the magnetic sensor 310 is mounted on the basis 110 so that the magnet 410 and the magnetic sensor 310 are disposed to face each other.

In addition, the magnet 410 may be mounted on the basis 110 and the magnetic sensor 310 may be mounted on the roof 240 of the cap 200 so that the magnet 410 and the magnetic sensor 310 are disposed to face each other.

As a more applied form, a form in which a plurality of magnets is provided is also possible, and this form will be described below with reference to FIGS. 4 and 5.

FIG. 4 is a schematic side cross-sectional view of a device for measuring grip strength according to one embodiment of the present invention, showing an exemplary form in which a plurality of magnets 410 and 420 is disposed.

First, as shown in FIG. 4, the magnets 410 and 420 are mounted on the roof 240. In addition, the magnets 410 and 420 are provided in plural, any one magnet 410 of the magnets 410 and 420 is disposed to face the magnetic sensor 310, and the magnets 410 and 420 may be arranged to be axially symmetric with respect to an imaginary axis of symmetry (SA) connecting the magnet 410 facing the magnetic sensor 310 and the magnetic sensor 310.

Alternatively, the magnets 410 and 420 may be provided in plural, and the magnets 410 and 420 may be disposed to be spaced apart from each other by a predetermined interval.

For reference, although not shown in the drawings, as a more applied form, a plurality of magnetic sensors may be disposed on the basis or the cap to detect change in a magnetic field corresponding to each of a plurality of magnets.

In addition, as shown in FIG. 5, another example in which a plurality of magnets is disposed is also possible.

FIG. 5 is a schematic side cross-sectional view of a device for measuring grip strength according to one embodiment of the present invention, showing another exemplary form in which a plurality of magnets is arranged.

As shown in FIG. 5, magnets 410, 420, and 430 are provided in plural, and any one magnet 410 of the magnets 410, 420, and 430 is disposed to face the magnetic sensor 310. In addition, the magnets 410, 420, and 430 may be arranged to be axially symmetric with respect to an imaginary axis of symmetry (SA) connecting the magnet 410 facing the magnetic sensor 310 and the magnetic sensor 310.

In addition, as shown in FIG. 5, preferably, a plurality of magnets 430 is disposed on the boundary wall 220, and the magnets 430 are disposed to be symmetrical with respect to the imaginary axis of symmetry (SA). In addition, among the magnets 430 disposed on the boundary wall 220 with the imaginary axis of symmetry (SA) therebetween, one magnet 430 and the other magnet 430 may be disposed to face each other.

In addition, the magnets 410, 420, and 430 may be provided in plural, and the magnets 410, 420, and 430 may be disposed to be spaced apart from each other by a predetermined interval.

For reference, although not shown in the drawings, as a more applied form, a plurality of magnetic sensors may be disposed on the basis, the roof, or the boundary wall to detect change in a magnetic field corresponding to each of a plurality of magnets.

In addition, a device for measuring grip strength according to another embodiment of the present invention will be described as follows. FIG. 6 is a schematic side cross-sectional view of a device for measuring grip strength according to another embodiment of the present invention.

Referring to FIG. 6, a device for measuring grip strength according to another embodiment of the present invention includes the basis 110, the cover 130, the magnet 410, the magnetic sensor 310, and the cap 200.

The basis 110 has a predetermined size to be held in the user's hand. The basis 110 is coupled to the cover 130 to form the pressure space 150.

In addition, the basis 110 is coupled to the cap 200 to support the cap 200. In addition, the basis 110 supports the magnetic sensor 310 or the magnet located inside the cap 200 and mounted on the basis 110. In the drawings, an example in which the magnetic sensor 310 is mounted on the basis 110 is shown.

In addition, the exhaust holes 115 through which air is exhausted from the sensing space 250 provided inside the cap 200 are formed in the basis 110.

The basis 110 is preferably made of a flexible material having elasticity, or may also be made of a hard material having hardness.

The cover 130 is coupled to the basis 110 to form the enclosed pressure space 150 separated from the outside. Preferably, the outer shape of the cover 130 is elastically deformed by grip strength applied by the user's hand.

Accordingly, the cover 130 may be made of a polymer having elasticity as a main material. The cap 200 is disposed between the basis 110 and the cover 130 and is coupled to the basis 110 to form the sensing space 250 separated from the pressure space 150.

As shown in FIG. 6, the lower ends of the cap 200 are coupled to the basis 110 to secure the sensing space 250 and to separate the magnet 410 and the magnetic sensor 310 from each other.

In addition, the cap 200 is configured to separate the sensing space 250 and the pressure space 150. The magnet 410 or the magnetic sensor is mounted on the cap 200. FIG. 6 shows an example in which the magnet 410 is mounted on the cap 200 and the magnetic sensor 310 is mounted on the basis 110.

In addition, it is also preferable that at least a portion of the cap 200 has a curved shape or a dome shape. In addition, the cap 200 is preferably made of a material having elasticity and ductility so that the cap 200 is elastically deformed by external force transmitted through air pressure in the pressure space 150.

In addition, the cap 200 that is elastically deformable may be made of the same material as the cover 130.

In addition, a portion of the cap 200 may be made of a material having elasticity and ductility so that the cap 200 is elastically deformed by external force, and the remaining portion of the cap 200 may be made of a material having hardness to suppress deformation due to external force.

In addition, the exhaust holes 115 for communicating the sensing space 250 with the outside are preferably provided in the basis 110 so that the volume of the sensing space 250 formed by the cap 200 is changed.

When the cover 130 receiving grip strength applied by a user is deformed inward, due to air pressure inside the pressure space 150, which is an enclosed space, force is applied toward the sensing space, which is the inside of the cap 200.

Preferably, air in the sensing space 250 is exhausted to the outside so that the sensing space 250 is elastically deformed by air pressure in the pressure space 150. Accordingly, air in the sensing space 250 may be exhausted to the outside through the exhaust holes 115 formed in the basis 110. The exhaust holes 115 may be provided in plural and formed in the basis 110.

In addition, the exhaust holes 115 provided in plural are preferably formed in the basis 110 to be arranged symmetrically with respect to the magnetic sensor 310 mounted on the basis 110.

The magnet 410 is mounted on the cap 200 or the basis 110, and forms a magnetic field in the sensing space 250.

The magnetic sensor 310 is mounted on the cap 200 or the basis 110, and detects change in a magnetic field formed by the magnet 410. When grip strength of a user is applied to the cover 130, the cap 200 receives force due to air pressure in the sealed pressure space 150.

As the cap 200 receives force, the cap 200 is deformed inwardly and the volume of the sensing space 250 is reduced. At this time, since air in the sensing space 250 is exhausted through the exhaust holes 115, the degree of elastic deformation of the cap 200 may be increased in proportion to the strength of applied force.

In addition, since the cap 200 is deformed by force, the distance or the positional posture between the magnetic sensor 310 and the magnet 410 is changed. Here, the positional posture is the same as described above.

As the distance or positional posture between the magnetic sensor 310 and the magnet 410 is changed, the magnetic sensor 310 detects change in a magnetic field. The magnetic sensor 310 detects the degree of change in a magnetic field, and based on this detection, user's grip strength may be measured.

Accordingly, preferably, the magnet 410 is mounted on the cap 200 and the magnetic sensor 310 is mounted on the basis 110 so that the magnet 410 and the magnetic sensor 310 are disposed to face each other.

In addition, the magnet 410 may be mounted on the basis 110 and the magnetic sensor 310 may be mounted on the cap 200 so that the magnet 410 and the magnetic sensor 310 are disposed to face each other.

As a more applied form, a form in which a plurality of magnets is provided is also possible, and this form will be described below with reference to FIGS. 7 and 8.

FIG. 7 is a schematic side cross-sectional view of a device for measuring grip strength according to another embodiment of the present invention, showing an exemplary form in which a plurality of magnets is arranged.

As shown in FIG. 7, the magnets 410 and 420 are mounted on the cap 200. In addition, the magnets 410 and 420 are provided in plural, and any one magnet 410 of the magnets 410 and 420 is disposed to face the magnetic sensor 310. With respect to an imaginary axis of symmetry (SA) connecting the magnet 410 facing the magnetic sensor 310 and the magnetic sensor 310, the magnets 410 and 420 are arranged to be axially symmetric.

Alternatively, the magnets 410 and 420 may be provided in plural, and the magnets 410 and 420 may be disposed to be spaced apart from each other by a predetermined interval.

For reference, although not shown in the drawings, as a more applied form, a plurality of magnetic sensors may be disposed on the basis or the cap to detect change in a magnetic field corresponding to each of a plurality of magnets.

In addition, as shown in FIG. 8, in terms of arrangement of the magnets 410, 420, and 430, another form is also possible.

FIG. 8 is a schematic side cross-sectional view of a device for measuring grip strength according to another embodiment of the present invention, showing another exemplary form in which a plurality of magnets is arranged.

As shown in FIG. 8, the magnets 410, 420, and 430 are provided in plural, and any one magnet 410 of the magnets 410, 420, and 430 is disposed to face the magnetic sensor 310. In addition, with respect to an imaginary axis of symmetry (SA) connecting the magnet 410 facing the magnetic sensor 310 and the magnetic sensor 310, the magnets 410, 420, and 430 are preferably arranged to be axially symmetric.

In addition, as shown in FIG. 8, the magnets 430 of the magnets 410, 420, and 430 are preferably mounted on the cap 200 to be disposed to be symmetrical with respect to the imaginary axis of symmetry (SA). Here, the magnets 430 are attached to the cap 200 so that the direction of a magnetic field line is perpendicular to the axis of symmetry (SA).

Among the magnets 430 disposed on the cap 200 with the imaginary axis of symmetry (SA) therebetween, any one magnet 430 and another magnet 430 are preferably disposed to face each other.

The magnets 410, 420, and 430 may be provided in plural, and the magnets 410, 420, and 430 may be disposed to be spaced apart from each other by a predetermined interval.

For reference, although not shown in the drawings, as a more applied form, a plurality of magnetic sensors may be mounted on the basis, the cap or, the boundary wall to detect change in a magnetic field corresponding to each of a plurality of magnets.

In addition, a device for measuring grip strength according to an applied embodiment of the present invention will be described as follows. FIG. 9 is a schematic side cross-sectional view of a device for measuring grip strength according to an applied embodiment of the present invention.

Referring to FIG. 9, a device for measuring grip strength according to another embodiment of the present invention includes a housing 100, the magnet 410, the magnetic sensor 310, and the cap 200.

When the housing 100 is gripped by the user's hand, the outer shape of the housing 100 may be elastically changed by grip strength. In addition, the enclosed pressure space 150 separated from the outside is formed in the housing 100 to maintain internal pressure.

In addition, the cap 200 is coupled to the inside of the housing 100 to support the cap 200. In addition, the housing 100 is configured to support the magnetic sensor 310 or the magnets mounted on the housing 100. FIG. 9 shows an example in which the magnetic sensor 310 is mounted on the housing 100.

In addition, the exhaust holes 115 through which air is exhausted from the sensing space 250 provided inside the cap 200 are formed in the housing 100. The exhaust holes 115 are preferably provided in plural.

The housing 100 is preferably made of a flexible material having elasticity.

That is, the outer shape of the housing 100 is preferably elastically changed by grip strength applied by the user's hand. Accordingly, the housing 100 may be made of a polymer having elasticity as a main material.

The cap 200 is coupled to the inside of the housing 100 to form the sensing space 250 separated from the pressure space 150.

As shown in FIG. 9, the cap 200 is configured to secure the sensing space 250, and the lower end of the cap 200 is coupled to the housing 100 to separate the magnet 410 and the magnetic sensor 310 from each other.

In addition, in the housing 100, the cap 200 is configured to separate the sensing space 250 and the pressure space 150. The magnet 410 or the magnetic sensor is mounted on the cap 200. FIG. 9 shows an example in which the magnet 410 is mounted on the cap 200 and the magnetic sensor 310 is mounted on the housing 100.

In addition, it is also preferable that at least a portion of the cap 200 has a curved shape or a dome shape. In addition, the cap 200 is preferably made of a material having elasticity and ductility so that the cap 200 is elastically deformed by external force transmitted through air pressure in the pressure space 150.

In addition, the cap 200 that is elastically deformable may be made of the same material as the housing 100.

In addition, a portion of the cap 200 may be made of a material having elasticity and ductility so that the cap 200 is elastically deformed by external force, and the remaining portion of the cap 200 may be made of a material having hardness to suppress deformation due to external force.

In addition, one or more exhaust holes 115 for communicating the sensing space 250 with the outside are preferably provided in the basis 110 so that the volume of the sensing space 250 formed by the cap 200 is changed.

When the cover 130 receiving grip strength applied by a user is deformed inward, due to air pressure inside the pressure space 150, which is an enclosed space, force is applied toward the sensing space 250, which is the inside of the cap 200.

Preferably, air in the sensing space 250 is exhausted to the outside so that the sensing space 250 is elastically deformed by air pressure in the pressure space 150. Accordingly, air in the sensing space 250 may be exhausted to the outside through the exhaust holes 115 formed in the basis 110.

When the exhaust holes 115 are formed in plural, the exhaust holes 115 are preferably formed in the housing 100 to be formed in a uniform arrangement.

The magnet 410 is mounted on the cap 200 or the housing 100, and forms a magnetic field in the sensing space 250.

The magnetic sensor 310 is mounted on the cap 200 or the housing 100, and detects change in a magnetic field formed by the magnet 410. When grip strength of a user is applied to the cover 130, the cap 200 receives force due to air pressure in the sealed pressure space 150.

As the cap 200 receives force, the cap 200 is deformed inwardly and the volume of the sensing space 250 is reduced. At this time, since air in the sensing space 250 is exhausted through the exhaust holes 115, the degree of elastic deformation of the cap 200 may be increased in proportion to the strength of applied force.

In addition, it is also preferable that the exhaust holes 115 provided in plural are formed in the basis 110 to be symmetric with respect to the magnetic sensor 310 mounted on the housing 100.

In addition, since the cap 200 is deformed by force, the distance or the positional posture between the magnetic sensor 310 and the magnet 410 is changed. Here, the positional posture is the same as described above.

As the distance or positional posture between the magnetic sensor 310 and the magnet 410 is changed, the magnetic sensor 310 detects change in a magnetic field. The magnetic sensor 310 detects the degree of change in a magnetic field, and based on this detection, user's grip strength may be measured.

Accordingly, preferably, the magnet 410 is mounted on the cap 200 and the magnetic sensor 310 is mounted on the basis 110 so that the magnet 410 and the magnetic sensor 310 are disposed to face each other.

In addition, the magnet 410 may be mounted on the housing 100 and the magnetic sensor 310 may be mounted on the cap 200 so that the magnet 410 and the magnetic sensor 310 are disposed to face each other.

As a more applied form, a form in which a plurality of magnets is provided is also possible, and this form will be described below with reference to FIG. 10.

FIG. 10 schematically illustrates a device for measuring grip strength according to an applied embodiment of the present invention, showing an exemplary form in which a plurality of magnets is arranged.

As shown in FIG. 10, the magnets 410 and 420 are mounted on the cap 200. In addition, the magnets 410 and 420 are provided in plural, and any one magnet 410 of the magnets 410 and 420 is disposed to face the magnetic sensor 310. With respect to an imaginary axis of symmetry (SA) connecting the magnet 410 facing the magnetic sensor 310 and the magnetic sensor 310, the magnets 410 and 420 are preferably arranged to be axially symmetric.

Alternatively, the magnets 410 and 420 may be provided in plural, and the magnets 410 and 420 may be disposed to be spaced apart from each other by a predetermined interval.

In addition, the magnets 410 and 420 may be mounted on the cap 200 so that the magnetic poles thereof are directed toward the magnetic sensor 310.

For reference, although not shown in the drawings, as a more applied form, to detect change in a magnetic field corresponding to each of a plurality of magnets, the magnetic sensors provided in plural may be disposed on the housing or the cap.

In addition, a device for measuring grip strength according to a modified embodiment of the present invention will be described with reference to FIGS. 11 and 12.

FIG. 11 is a schematic side cross-sectional view of a device for measuring grip strength according to a modified embodiment of the present invention.

Referring to FIG. 11, the device for measuring grip strength according to a modified embodiment of the present invention includes the cap 200 including the boundary wall 220 and the roof 240, the housing 100, the magnet 410, and the magnetic sensor 310.

First, when the housing 100 is gripped by the user's hand, the outer shape of the housing 100 may be elastically changed by grip strength. In addition, the enclosed pressure space 150 separated from the outside is formed in the housing 100 to maintain internal pressure.

In addition, the cap 200 is coupled to the inside of the housing 100, and the housing 100 is configured to support the boundary wall 220 of the cap 200. In addition, the housing 100 is configured to support the magnetic sensor 310 or the magnet mounted on the housing 100. FIG. 11 shows an example in which the magnetic sensor 310 is mounted on the housing 100.

In addition, the exhaust holes 115 through which air is exhausted from the sensing space 250 provided inside the boundary wall 220 of the cap 200 and the roof 240 are formed in the housing 100. The exhaust holes 115 may be provided in plural.

The housing 100 is preferably made of a flexible material having elasticity.

That is, the outer shape of the housing 100 is preferably elastically changed by grip strength applied by the user's hand. Accordingly, the housing 100 may be made of a polymer having elasticity as a main material.

The cap 200 is coupled to the inside of the housing 100, and forms the sensing space 250 separated from the pressure space 150. The cap includes the boundary wall 220 and the roof 24.

As shown in FIG. 11, the cap 200 including the boundary wall 220 and the roof 240 secures the sensing space 250, and the lower end of the boundary wall 220 is coupled to the housing 100 to separate the magnet 410 and the magnetic sensor 310 from each other.

In addition, the roof 240 of the cap 200 is coupled to the upper end of the boundary wall 220 to separate the sensing space 250 and the pressure space 150. The magnet 410 or the magnetic sensor is mounted on the roof 240 of the cap 200.

FIG. 11 shows an example in which the magnet 410 is mounted on the roof 240 of the cap 200 and the magnetic sensor 310 is mounted on the housing 100.

In addition, it is also preferable that at least a portion of the cap 200 including the boundary wall 220 and the roof 240 has a curved shape or a dome shape.

In addition, the cap 200 including the boundary wall 220 and the roof 240 is preferably made of a material having elasticity and ductility to be elastically deformed by external force transmitted through air pressure in the pressure space 150.

For example, the roof 240 of the cap 200 is preferably made of a material having elasticity and ductility to be elastically deformed by external force, and the boundary wall 220 of the cap 200 is preferably made of a material having hardness to suppress deformation due to external force.

Alternatively, it is also preferable that the roof 240 and the boundary wall 220 of the cap 200 are made of a material having elasticity and ductility to be elastically deformed by external force.

In addition, the roof 240 of the cap 200 that is elastically deformable is preferably formed of the same material as the housing 100.

In addition, one or more exhaust holes 115 for communicating the sensing space 250 with the outside are preferably provided in the housing 100 so that the volume of the sensing space 250 formed by the cap 200 is changed.

In addition, it is also preferable that the exhaust holes 115 provided in plural are formed in the basis 110 to be symmetric with respect to the magnetic sensor 310 mounted on the housing 100.

When the housing 100 is deformed inward by grip strength applied by a user, due to air pressure inside the enclosed pressure space 150, force is applied toward the sensing space 250 inside the cap 200.

Preferably, air in the sensing space 250 is exhausted to the outside so that the sensing space 250 is elastically deformed by air pressure in the pressure space 150. Accordingly, air in the sensing space 250 may be exhausted to the outside through the exhaust holes 115 formed in the basis 110.

When the exhaust holes 115 are formed in plural, the exhaust holes 115 are preferably formed in the housing 100 to be formed in a uniform arrangement.

The magnet 410 is mounted on the cap 200 or the housing 100, and forms a magnetic field in the sensing space 250.

The magnetic sensor 310 is mounted on the cap 200 or the housing 100, and detects change in a magnetic field formed by the magnet 410. When grip strength of a user is applied to the cover 130, the cap 200 receives force due to air pressure in the sealed pressure space 150.

As the cap 200 receives force, the cap 200 is deformed inwardly and the volume of the sensing space 250 is reduced. At this time, since air in the sensing space 250 is exhausted through the exhaust holes 115, the degree of elastic deformation of the cap 200 may be increased in proportion to the strength of applied force.

In addition, since the cap 200 is deformed by force, the distance or the positional posture between the magnetic sensor 310 and the magnet 410 is changed. Here, the positional posture is the same as described above.

As the distance or positional posture between the magnetic sensor 310 and the magnet 410 is changed, the magnetic sensor 310 detects change in a magnetic field. The magnetic sensor 310 detects the degree of change in a magnetic field, and based on this detection, user's grip strength may be measured.

Accordingly, it is also preferable that the magnet 410 is mounted on the roof 240 of the cap 200 and the magnetic sensor 310 is mounted on the housing 100 so that the magnet 410 and the magnetic sensor 310 are disposed to face each other.

In addition, it is also preferable that the magnet 410 is mounted on the housing 100 and the magnetic sensor 310 is mounted on the roof 240 of the cap 200 so that the magnet 410 and the magnetic sensor 310 are disposed to face each other.

As a more applied form, a form in which a plurality of magnets is provided is also possible, and this form will be described below with reference to FIG. 12.

FIG. 12 is a schematic side cross-sectional view of a device for measuring grip strength according to a modified embodiment of the present invention, showing an exemplary form in which a plurality of magnets is arranged.

As shown in FIG. 12, the magnets 410 and 420 are mounted on the roof 240 of the cap 200, and a plurality of magnets 430 is mounted on the boundary wall 220 of the cap 200.

In addition, the magnets 410, 420, and 430 are provided in plural, and any one magnet 410 of the magnets 410 and 420 is disposed to face the magnetic sensor 310. With respect to an imaginary axis of symmetry (SA) connecting the magnet 410 facing the magnetic sensor 310 and the magnetic sensor 310, the magnets 410, 420, and 430 are preferably arranged to be axially symmetric.

Alternatively, the magnets 410, 420, and 430 are provided in plural, and the magnets 410, 420, and 430 are preferably disposed to be spaced apart from each other by a predetermined interval.

The magnets 410, 420, and 430 may be mounted on the roof 240 or the boundary wall 220 so that the magnetic poles thereof are directed toward the magnetic sensor 310.

For reference, the magnets 430 may not be mounted on the boundary wall 220, and the magnets 410 and 420 may be mounted only on the roof 240.

In addition, although not shown in FIG. 12, as a more applied form, a plurality of magnetic sensors may be mounted on the housing, the roof, or the boundary wall to detect change in a magnetic field corresponding to each of a plurality of magnets.

As described above, since a device for measuring grip strength according to the present invention senses magnetic field change caused by grip strength applied by the hand, ease and accuracy may be secured when measuring grip strength.

As described above, the detailed description of the present invention has been made by the embodiments with reference to the accompanying drawings. However, since the above-described embodiments have only been described with reference to preferred embodiments of the present invention, it should not be construed that the present invention is limited to the above-described embodiments, and the scope of the present invention is defined by the claims and the equivalent concept.

The invention claimed is:

1. A device for measuring grip strength, comprising:
   a basis;
   a cover coupled to the basis to form an enclosed pressure space separated from outside, wherein an outer shape of the cover is elastically changed by grip strength;
   a cap disposed between the basis and the cover and coupled to the basis to form a sensing space separated from the pressure space;
   magnets mounted on the cap or the basis to form a magnetic field in the sensing space; and
   a magnetic sensor mounted on the cap or the basis to detect change in the magnetic field formed by the magnet.

2. The device according to claim 1, wherein the cap comprises a boundary wall having a lower end coupled to the basis to secure the sensing space; and a roof coupled to an upper end of the boundary wall to separate the sensing space and the pressure space, and on which the magnets or the magnetic sensor is mounted.

3. The device according to claim 1, wherein at least a portion of the cap has a curved shape or a dome shape, and is made of a material that is elastically deformable.

4. The device according to claim 1, wherein exhaust holes for communicating the sensing space with an outside are provided in the basis to change a volume of the sensing space.

5. The device according to claim 1, wherein the device for measuring grip strength has any one arrangement structure of an arrangement structure in which the magnets are mounted on the cap and the magnetic sensor is mounted on the basis and an arrangement structure in which the magnets are mounted on the basis and the magnetic sensor is mounted on the cap, so that the magnets and the magnetic sensor are disposed to face each other.

6. The device according to claim 5, wherein the magnets are provided in plural, and any one of the magnets is disposed to face the magnetic sensor; and
the magnets are arranged to be axially symmetric with respect to an imaginary axis of symmetry connecting the magnet facing the magnetic sensor and the magnetic sensor.

7. The device according to claim 5, wherein the magnets are provided in plural, and the magnets are disposed to be spaced apart from each other by a predetermined interval.

8. The device according to claim 2, wherein the device for measuring grip strength has any one arrangement structure of an arrangement structure in which the magnets are mounted on the roof and the magnetic sensor is mounted on the basis and an arrangement structure in which the magnets are mounted on the basis and the magnetic sensor is mounted on the roof, so that the magnets and the magnetic sensor are disposed to face each other,
wherein the magnets are provided in plural, and one or more of the magnets are disposed on the boundary wall.

9. The device according to claim 8, wherein the boundary wall of the cap is made of a material having elasticity and ductility to be elastically deformed by external force.

10. The device according to claim 8, wherein the roof of the cap is made of a material having elasticity and ductility to be elastically deformed by external force, and
the boundary wall of the cap is made of a material having hardness to suppress deformation due to external force.

11. A device for measuring grip strength, comprising: a basis;
a housing having an outer shape that is elastically changed by grip strength applied when gripped by a user's hand, wherein an enclosed pressure space separated from outside is formed in the housing to maintain internal pressure;
a cap coupled to an inside of the housing to form a sensing space separated from the pressure space;
magnets mounted on the cap or the housing to form a magnetic field in the sensing space; and
a magnetic sensor mounted on the cap or the housing to be spaced apart from the magnets, and configured to detect change in the magnetic field according to change in position or posture relative to the magnets.

12. The device according to claim 11, wherein at least a portion of the cap has a dome shape, and is made of a material having elasticity.

13. The device according to claim 11, wherein the cap comprises a boundary wall having a lower end coupled to an inside of the housing to secure the sensing space and separate the magnets and the magnetic sensor; and
a roof coupled to an upper end of the boundary wall to separate the sensing space and the pressure space, and on which the magnets or the magnetic sensor is mounted.

14. The device according to claim 11, wherein exhaust holes for communicating the sensing space with an outside are provided in the housing so that a volume of the sensing space is changed.

15. The device according to claim 11, wherein the device for measuring grip strength has any one arrangement structure of an arrangement structure in which the magnets are mounted on the cap and the magnetic sensor is mounted on the housing and an arrangement structure in which the magnets are mounted on the housing and the magnetic sensor is mounted on the cap, so that the magnets and the magnetic sensor are disposed to face each other.

16. The device according to claim 15, wherein the magnets are provided in plural, and any one of the magnets is disposed to face the magnetic sensor; and
the magnets are arranged to be axially symmetric with respect to an imaginary axis of symmetry connecting the magnet facing the magnetic sensor and the magnetic sensor.

17. The device according to claim 15, wherein the magnets are provided in plural, and the magnets are disposed to be spaced apart from each other by a predetermined interval.

18. The device according to claim 13, wherein the device for measuring grip strength has any one arrangement structure of an arrangement structure in which the magnets are mounted on the roof and the magnetic sensor is mounted on the basis and an arrangement structure in which the magnets are mounted on the basis and the magnetic sensor is mounted on the roof, so that the magnets and the magnetic sensor are disposed to face each other,
wherein the magnets are provided in plural, and one or more of the magnets are disposed on the boundary wall.

19. The device according to claim 18, wherein the boundary wall of the cap is made of a material having elasticity and ductility to be elastically deformed by external force.

20. The device according to claim 18, wherein the roof of the cap is made of a material having elasticity and ductility to be elastically deformed by external force, and
the boundary wall of the cap is made of a material having hardness to suppress deformation due to external force.

* * * * *